United States Patent [19]

Turner et al.

[11] Patent Number: 4,967,765

[45] Date of Patent: Nov. 6, 1990

[54] URETHRAL INSERTED APPLICATOR FOR PROSTATE HYPERTHERMIA

[75] Inventors: Paul F. Turner; Theron N. Schaefermeyer, both of North Salt Lake; Amer M. Tumeh, Salt Lake City; Trung V. Nguyen, Murray, all of Utah

[73] Assignee: BSD Medical Corporation, Salt Lake City, Utah

[21] Appl. No.: 225,307

[22] Filed: Jul. 28, 1988

[51] Int. Cl.$^5$ .............................................. A61N 5/02
[52] U.S. Cl. .................................. 128/785; 128/786; 128/804; 128/736
[58] Field of Search ........................ 128/804, 784–786, 128/736, 401

[56] References Cited

U.S. PATENT DOCUMENTS

| | | | |
|---|---|---|---|
| 4,154,246 | 5/1979 | LeVeen | 128/804 |
| 4,311,154 | 1/1982 | Sterzer | 128/804 |
| 4,583,556 | 4/1986 | Hines et al. | 128/784 |
| 4,601,296 | 9/1986 | Yerushalmi | 128/804 |
| 4,658,836 | 4/1987 | Turner | 128/804 |
| 4,681,122 | 7/1987 | Winters et al. | 128/736 |
| 4,700,716 | 10/1987 | Kasevich et al. | 128/804 |
| 4,813,429 | 3/1989 | Eshel et al. | 128/736 |

FOREIGN PATENT DOCUMENTS 8103616 12/1981 World Int. Prop. O. .......... 128/804

OTHER PUBLICATIONS

Dunsconde et al., "Heat Production . . . Thermocouples", Med. Phys. 13(4), Jul./Aug. 1986, pp. 457–461.
Constable et al, "Perturbation . . . Thermometer", Med. Phys. 14131, May/Jun. 1987, pp. 385–388.
Tadashi Harada, et al., "Microwave Surgical Treatment of Diseases of Prostate", Urology, Dec. '85, vol. XXVI, No. 6, pp. 572–576.
Ding Jen Lee, et al., "A New Design of Microwave Interstitial Applicators for Hyperthermia with Improved Treatment Volume", Nov. '86, Int. J. Radiation Oncology Biol. Phys, vol. 12, pp. 2003–2008.
Ding-Jiu Li, et al., "Design & Thermometry of an Intracavitary Microwave Applicator Suitable for Treatment of Some Vaginal & Rectal Cancers", Nov. '84, Int. J. Radiation Oncology Boil. Phys., vol. 10, pp. 2155–2161.
Leonid Leybovich, et al., "Intracavitary Hyperthermia: A Newly Designed Applicator for Tracheal Tumors", Jan. '87, Endocurietherapy/Hyperthermia Oncology, vol. 3, pp. 23–29.
Andrew Wu, et al., "Perfrmance Characteristics of a Helical Microwave Interstitial Antenna for Local Hyperthermia", Mar./Apr. '87, Med. Phys, 14(2), pp. 235–237.
El-Deek M. El-Sayed et al., "Use of Sheath Helix Slow-Wave Structure as an Applicator in Microwave Heating Systems", 1981, Journal of Microwave Power, 16 (3 and 4), pp. 283–288.
Jozef Mendecki et al., "Microwave Applicators for Localized Hyperthermia Treatment of Cancer of the Prostate", Nov. '80, Int. J. Radiation Boil. Phys., vol. 6, No. 11, pp. 1583–1588.
A. Yerushalmi et al., "Localized Microwave Hyperthermia in the Treatment of Poor Operative Risk Patients with Benign Prostatic Hyperplasia", May '85, Williams & Wilkins, Co. vol. 133, pp. 873–876.

*Primary Examiner*—Lee S. Cohen
*Attorney, Agent, or Firm*—Mallinckrodt & Mallinckrodt

[57] ABSTRACT

A urethral inserted applicator for prostate hyperthermia includes a multi-tube, balloon type catheter. The catheter includes first and second closed end fluid dry tubes, respectively, for a helical coil antenna type applicator, and a microwave type temperature sensor for measuring the temperature of the prostate tissue, and an open fluid receiving tube. A microwave generator supplies electromagnetic energy to the applicator. A comparator is connected to the temperature sensor and a temperature reference potentiometer for comparing the actual tissue temperature level with a desired temperature level and outputting control signals to the microwave generator for controlling the output to the applicator. The coil type applicator is an elongated coil having a tip end connected to the center conductor of a coaxial cable and an opposite end connected to the outer conductor of the coaxial cable. A sheet or sheath of insulation material covers the coil antenna for insulating the coil from the tissue and the thickness of the sheet may be varied to provide uniform tissue heating along the length of the coil. The balloon of the catheter engages the body's bladder to position the applicator properly during the treatment.

17 Claims, 5 Drawing Sheets

URETHRAL INSERTED APPLICATOR FOR PROSTATE HYPERTHERMIA

This invention relates to electromagnetic radiation devices for medical hyperthermic purposes, and more particularly to a combined catheter and microwave applicator for treating benign prostatic hypertrophy by urethral insertion.

BACKGROUND OF THE INVENTION

Hyperthermia or induced high body temperature has been considered beneficial in treating various human diseases including many types of cancer. More specifically, various types of malignant growths are considered by many researchers to have a relatively narrow hyperthermia treatment temperature range. Below a threshold temperature of about 41.5 degrees Celsius, thermal destruction of these malignancies is not possible, and in fact their growth may be stimulated. However, at temperatures above a range of about 43 to 45 degrees Celsius thermal damage to most normal body tissue cells occurs if exposure lasts for even a relatively short duration.

While some types of skin cancers are known to respond to direct application of surface heat, deeply located malignant growths, owing to normal blood flow body heat transfer properties of the body, were most difficult to heat to the desired temperature without damaging overlying healthy tissue. A solution to this problem has been the development of electromagnetic radiation (EMR) heating devices for inducing hyperthermia. This form of treatment is known as "diathermia".

EMR heating of subsurface growths from an exterior surface is ordinarily enabled by configuration and placement of one or more applicators and by appropriate selection of EMR frequency, phase and intensity. Nevertheless, tissue growths inside of, or in close proximity to, heat sensitive tissue or organs, are much more effectively and safely heated by EMR irradiating applicators positioned within the body as closely as possible to the growth requiring treatment.

The advantages of positioning EMR applicators relatively close to the growth to be heated by radiation include improved heating control, more localized heating and consequently less possibility of overheating adjacent healthy tissue and more direct treatment of the enlarged tissues causing the undesireable symptoms.

Close applicator access to certain types of diseased tissue growths is provided by surgical procedures for naturally occurring body passages such as the esophagus, larynx, prostate gland and colon. Surgical procedures enlarge the passage by cutting away the passage tissue. Some heating methods are placing over the tissue or in an incision small EMR applicators to provide direct irradiation of the growth. An illustrative type of a body passage insertable EMR applicator is described in U.S. Pat. No. 2,407,690 issued to Southworth. The Southworth type body passage EMR applicators have been configured in a manner causing a heating pattern that tends to be concentrated at the radiating tip of the applicator and which decreases at a usually exponential rate from such tip towards the radiation source.

Special and difficult problems often attend growths found along natural body passages. For example, diseased tissue tends to spread around and along the passage, often in a relatively thin layer Typically, the diseased layer may be less than a centimeter thick and may extend as far as 6-10 centimeters along the passage. The use of Southworth type applicators result in nonuniform irradiation heating of the elongated growth. Thus, the temperature at the tip may have to be so hot that it kills surrounding healthy tissue in order to make the tip towards the power supply hot enough to kill the growth.

Ridged and nonflexible antenna rectal inserted devices are known. Examples of such devices are disclosed in U.S. Pat. No. 4,601,296 issued to Yerushalmi, and a 1980 article titled "Microwave Applicators for Localized Hyperthermia Treatment of Cancer of the Prostate" by Mendecki et al., Int. J. Radiation Oncology, Biol. Phys., Vol. 6, pp. 1583 and 1588.

Also, helical coil designs have been used to heat tissues placed within the cylindrical opening of the device. Such devices are disclosed in U.S. Pat. No. 4,527,550 issued July 1985 to Ruggera.

A body passage insertable applicator apparatus for EMR systems is known that includes a urethral inserted probe having a monopole antenna (Microwave Surgical Treatment of Diseases of Prostate, Harada et al., Urology, December 1985, Vol. XXVI, No. 6, pp. 572-576). Also known is a helical wound coil applicator having coaxial inner and outer conductors electrically connected at an EMR input end to a conventional coaxial transmission line for transmitting high frequency EMR from a source to the applicator. The applicator outer conductor is longitudinally split on opposite sides to form first and second outer conductor segments. The inner conductor is electrically connected to an applicator termination end of one of such segments. A dielectric media is disposed between the applicator inner and outer conductors, and the outer conductor and termination end are covered by a dielectric sheath. A substantially uniform, external electric tissue heating field is obtained along substantially the entire length of the applicator by exponentially increasing the thickness of the dielectric sheath towards the termination end and making the thickness of the sheath over the termination end equal to at least half the outer diameter of the applicator. Those persons skilled in the art desiring further information concerning this device are referred to U.S. Pat. No. 4,658,836 issued Apr. 21, 1987 to Paul F. Turner.

A principal feature distinguishing the present invention from the prior art devices is the provision of urethral insertable EMR applicator principally adapted for benign prostatic hyperplasia (BPH), which provides the generally cylindrical or longitudinally uniform EMR heating pattern necessary to enable substantially uniform heating of BPH growths or other tissue diseases associated with the urinary track.

SUMMARY OF THE INVENTION

Accordingly, it is an object of the invention to provide an improved treatment of benign prostatic hyperplasis as well as other diseases of the prostate gland locally involved around the urethra.

Another object of the invention is to provide an EMR applicator apparatus meeting the clinical requirements of high flexibility, sterilization, disposability, low cost, urinary drainage, and integral temperature monitoring along the perimeter of the urethral wall.

Yet another object of the invention is to provide an urethral insertable EMR applicator which provides the generally cylindrical or longitudinally uniform EMR heating pattern necessary to enable substantially uniform heating of BPH growths or other tissue diseases associated with the urinary track.

A further object of the invention is to provide an urethral insertable EMR applicator which can be positioned with respect to the prostate and maintained against movement therefrom during treatment.

Briefly stated the urethral insertable EMR applicator system includes a controlled source of EMR connected to an electrical coiled conductor housed in a catheter. A temperature controller includes at least one sensor for determining the temperature of the surrounding tissue and generating control signals for the source of EMR.

The catheter includes an applicator positioning means for automatically positioning the coiled conductor adjacent the prostate gland and for maintaining the position during the treatment. The electrical coil is suitably sheathed to provide an external substantially uniform electric tissue heating field to be radiated at nearly all transverse cross sections along the applicator for substantially uniform tissue heating.

Advantages of the present invention is the provision of a low cost, disposable applicator which is detachably connected to a modified balloon type catheter for the treatment of BPH. BPH is usually treated by surgery with significant side effects. These side effects include hemorrhage, impotency, anesthetic complications, and technical failures. The use of the combined applicator catheter apparatus involves a treatment which requires no anesthesia or surgery and requires only 1 or 2 hour office visits to accomplish in comparison to post surgical hospitalization.

BRIEF DESCRIPTION OF THE DRAWINGS

Other objects and features of the invention will become more readily apparent from the following detailed description when read in conjunction with the accompanying drawings, in which.

DETAILED DESCRIPTION OF A PREFERRED EMBODIMENT

Figures 1, 2:
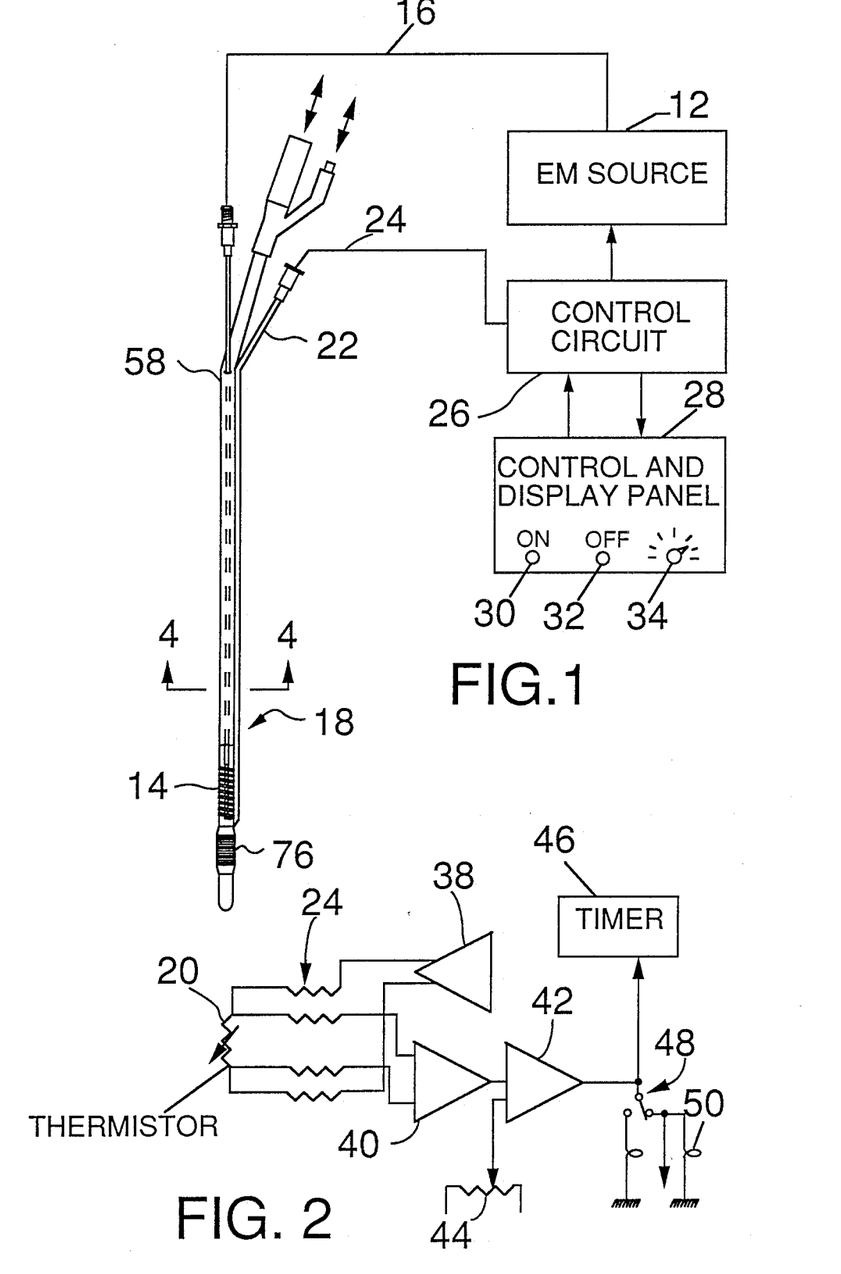
FIG. 1 is a view of the urethral insertable EMR applicator system showing the schematic diagram in block form.
FIG. 2 is a functional schematic view of the temperature sensor and microwave source control functional circuits.

Referring now to FIG. 1, the urethral insertable electromagnetic radiation (EMR) applicator system includes an electromagnetic energy source 12 having an oscillator for supplying a maximum 40 watts electrical power at a 915 MHz frequency, for example, to an antenna 14 through a coaxial cable 16. A suitable cable is a typical RG-178B cable or one of equivalent size. The antenna 14 is a microwave helical coil mounted in a catheter 18 with the end farthest from the power source 12 soldered to the tip of the solid inner conductor and the end closest to the power source soldered to the outer braided conductor of the coaxial cable. The catheter 18 is for example a size 12 French catheter modified as hereinafter described.

The coil of antenna 14 may contain one or more of the following physical features:

(a) open connection to the tip of the coil and center coaxial conductor;

(b) open connection to the base of the coil and the outer coaxial conductor;

(c) conductor breaks or gaps within the coil winding;

(d) multiple wrapped coils co-located at the same zone;

(e) multiple coils stacked longitudinally and connected to individual coaxial cables to allow modification of the heat pattern length using either coherent or non-coherent phase energy into each coil;

(f) straight but flexible conductors rather than coiled conductors;

(g) a coil with progressively increasing conductor width towards the tip of the applicator;

(h) a coil with different turns ratio per unit length;

(i) diameter variations of the center conductor within the coil length; and (j) modification of the dielectric material or thickness around the center conductor or coil antenna. A separable insulated temperature sensor 20 (FIG. 2) is inserted in a flexible tube 22 (FIG. 1) during treatment. The tube is attached exteriorly of the catheter 16 adjacent to the antenna 14. The temperature sensor measures the temperature of the tissue surrounding the catheter. The temperature sensor is connected by an insulated four resistive lead cable 24 to a temperature sensor circuit and microwave power source control circuit 26. While a single tube 22 and corresponding temperature sensor 20 are illustrated, it will be readily appreciated by those skilled in this art that more than one tube 22 and associated temperature sensor 20 could be utilized if desired.

The microwave power source control circuit has its output connected to the microwave energy source 12 for maintaining a power supply sufficient to maintain a tissue temperature between about 41.5 degree Celsius to about 47 degree Celsius. A control and display panel 28 is connected to the temperature sensor circuit and microwave control circuit 26 for two way communication. The control and display panel 28 includes EMR energy on/off switch buttons 30 and 32, and a temperature controller 34 for setting the desired operating temperature for the temperature sensor circuit and microwave control.

The temperature sensor circuit (FIG. 2) of the temperature sensor circuit and microwave control circuit 26 (FIG. 1) includes the temperature sensor 20 which may be a typical precalibrated thermistor sensor connected to a constant current source 38. An amplifier 40 is connected to the thermistor 20 for amplifying the thermistor output to a working level. A high gain comparator 42 has input terminals connected to the amplifier 40 and to a temperature setting potentiometer 44 of the temperature controller 34 located on the control and display panel 28 (FIG. 1) for comparing the amplified thermistor output with a desired temperature reference voltage and outputting switch control signals. The high gain comparator 42 (FIG. 2) has its output connected to the junction of a timer 46 and an electrically controlled pole of a double pole switch 48. A secondary temperature sensor 20, lead 24 and control circuit 26 can be added for a redundant monitor. This could be inserted into other tissue or in a second flexible tube 22.

The timer 46 is the EMR power source control. The timer is triggered in response to the initial receipt of power from the comparator 42 for measuring a preselected treatment time, and at the end of the timing period cuts off the microwave power source. In addition, the pole of the switch 48 is manually controlled by the switch control on/off buttons 30 and 32. When the switch is positioned on, as shown, a control signal is output on lead 50 to power on the microwave power source; conversely when the switch 48 is turned to the Off position the EMR power source is turned off. It should be noted the timer 46, comparator 42, temperature setting potentiometer 44, control switch 48, and portions of the control circuit can be replaced by a small computer chip operating in an equivalent manner.

While a representative preferred embodiment of the microwave control circuit 26, the control and display panel 28 and the temperature sensor circuit has been illustrated and described herein, it will be readily apparent to those skilled in this art that a variety of modifications could be made to this overall control system if desired. For example, at least a portion of the illustrated circuitry could be replaced with a minicomputer system or otherwise automated if desired.

Figure 3:
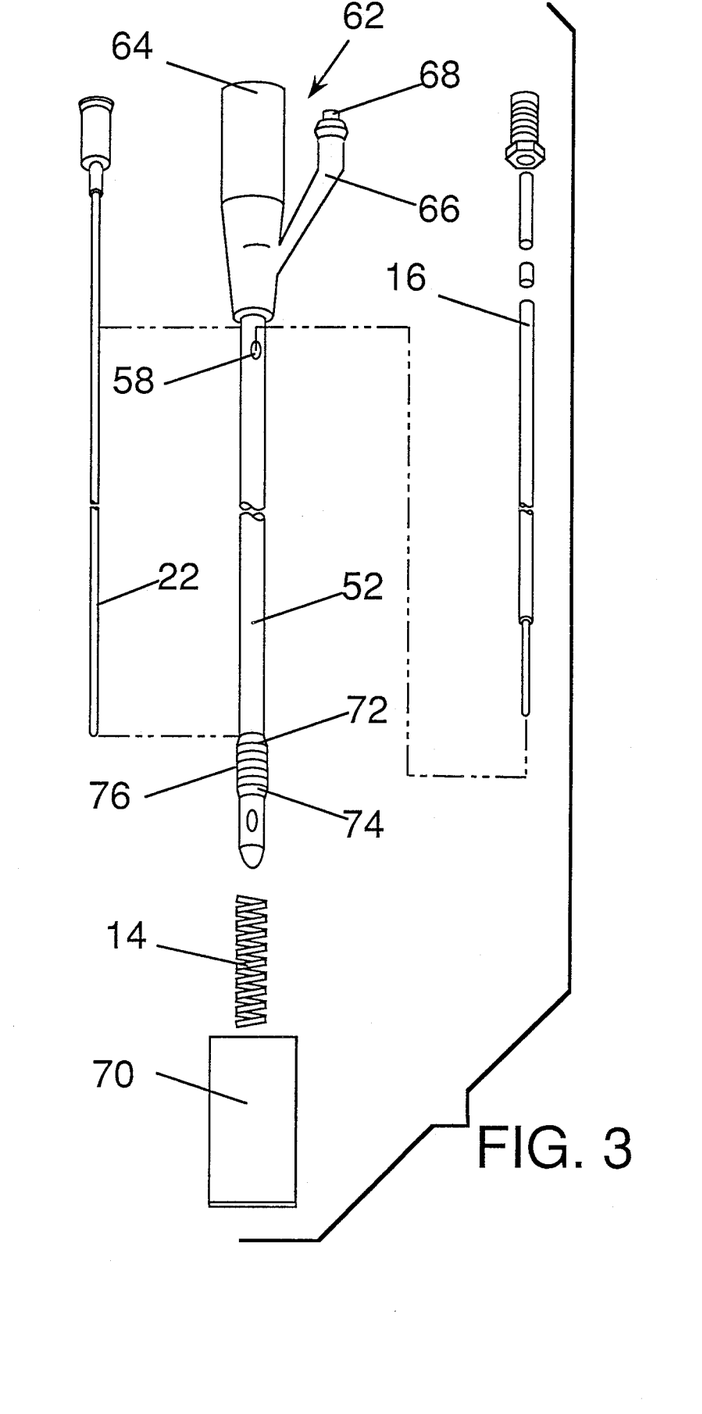
FIG. 3 is an exploded view of the urethral insertable EMR applicator.
Figure 4:
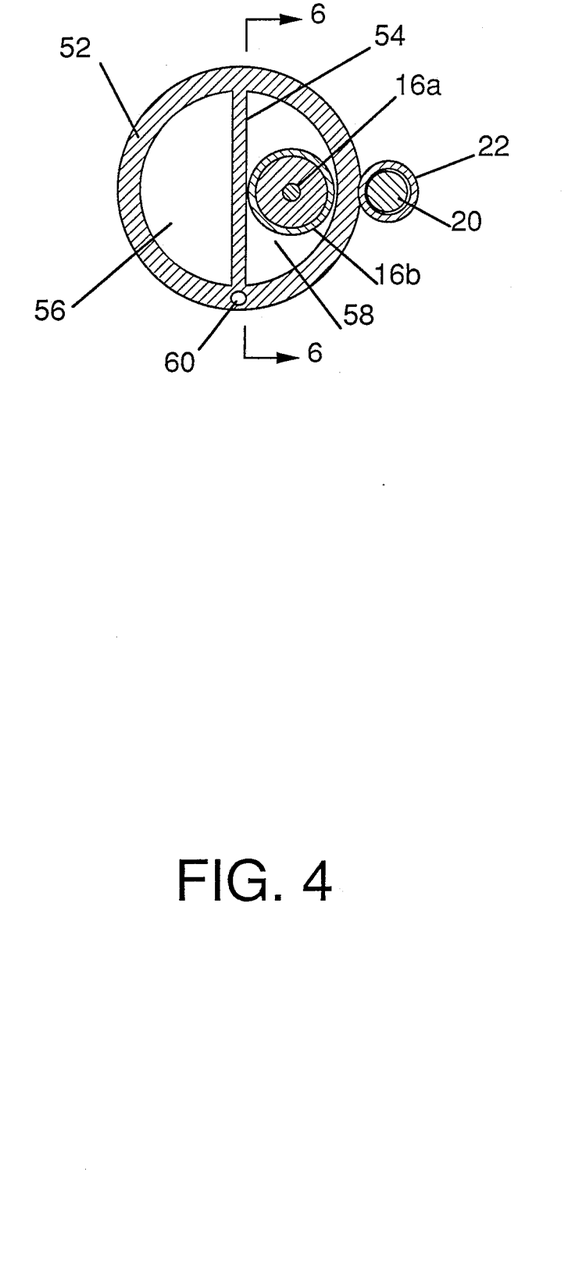
FIG. 4 is a cross sectional view of the urethral insertable EMR applicator taken along line 4—4 of FIG. 1.

The catheter 18 of the combined catheter and applicator is, for example, a balloon type urological catheter having a flexible, plastic tubular body 52 (FIGS. 3 and 4) which is divided by a partition 54 (FIG. 4) into a catheter drainage tube 56 and a fluid isolated tube 58, and has walls forming an air or fluid passage 60 for inflating balloon 76. The flexible tube 22 for the temperature sensor is attached exteriorly of the tubular body 52. The tubular body 52 has a bifurcated opening piece 62 having one side 64 for connecting the central drainage tube 56 to a waste receiving receptacle, and a second side 66 having an air or fluid input/output valve 68 for connecting the air or fluid passage 60 to a pressurized air or fluid supply source to inflate the balloon 76 after insertion. This air or fluid supply source could simply be a syringe.

The coaxial cable 16 (FIG. 3) passes through the fluid isolated tube 58 through outlets adjacent ends of the antenna forming coil to connect to the antenna coil 14 as previously described. A dielectric sheet 70 or tube, such as, for example, a silicone rubber, is placed and bonded over the spiral metal coil 14 to complete the applicator. The sheath 70 is the means for causing the external, electric tissue heating field to be substantially uniform along the length of the applicator. The thickness of the sheath may be varied exponentially if necessary to obtain the uniform heating field. The coil 14 is positioned against a stop 72 of a pair of spaced stops 72 and 74 formed on the tubular body 52. A 5 cc ribbed balloon 76 is positioned between the stops 72 and 74 in open communication with the outlet of the air or fluid passage 60. Thus, when the catheter is positioned so that the balloon, when inflated, is resting on the neck of the bladder, the applicator is properly positioned with respect to the prostate gland and free from movement for the duration of the hyperthermic treatment.

Figure 6:
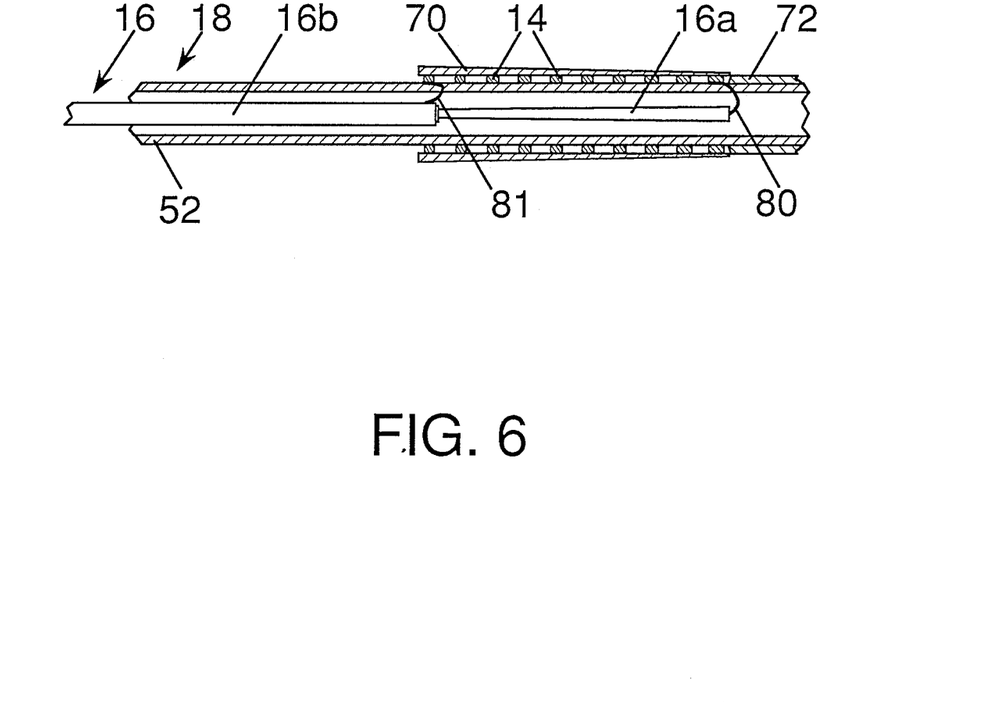
FIG. 6 is a fragmentary section taken on the line 6—6 of FIG. 4 showing an embodiment of the coaxial conductor, coil, and dielectric material covering the coil.

FIG. 6 shows an embodiment of the coaxial cable wherein the center coaxial conductor 16a extends through the center of the coil and is tapered to a larger diameter at its end. Coil 14 has a coil conductor width which increases toward the insertion tip end of the catheter. The dielectric insulation 70 varies in thickness and tapers along its length so is thinner toward the insertion end of the catheter. The end of the coil toward the insertion tip of the catheter is connected by wire 80 to the center coaxial conductor 16a and the opposite end of the coil is connected by wire 81 to the outer coaxial conductor 16b. The various changes in dimensions are shown greatly exaggerated so as to be visible. While variations g, i, and j listed on page 7 are illustrated together in FIG. 6, any of the variations may be used along or in various other combinations to provide desired characteristics of the applicator.

In operation, with the catheter properly positioned as described above, and the timer 46 and the temperature set dial set as desired, the EMR oscillator 12 is turned on by RF switch 30 and the applicator 14 radiates power into the area of the prostate gland until the desired temperature is reached; when reached the comparator 42 outputs control signals to the oscillator to manipulate its EMR output power to maintain the temperature substantially constant for the selected treatment time period. At the end of the treatment time, the oscillator is automatically turned off, but the oscillator can be turned off at any time using the RF off switch 32.

Figure 5:
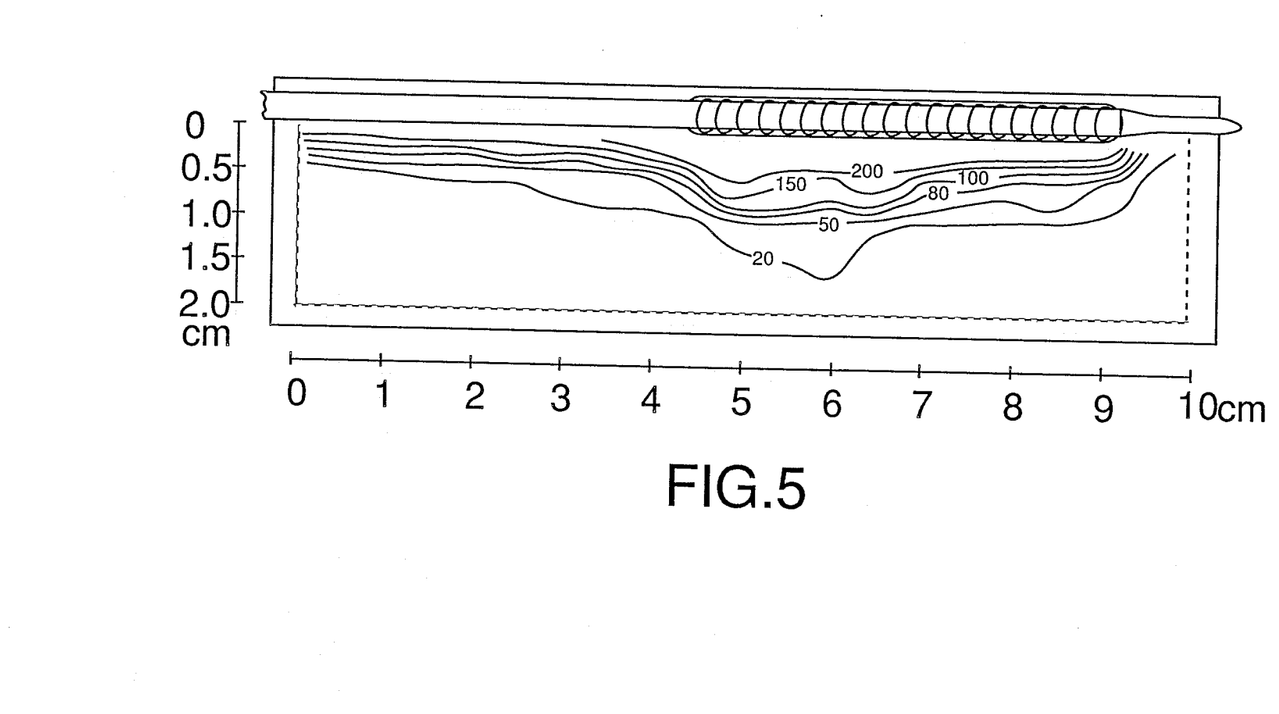
FIG. 5 is a view showing the SAR distribution of the prostate applicator.

The apparatus was tested using muscle equivalent phantom material having a relative dielectric=69.0 and conductivity=1.4 mho/m to simulate prostate tissues and the Iso-SAR (specific-absorption-rate) distribution of applicator curves charted as shown in FIG. 5. The test parameters were as follows: Frequency=915 MHz
SAR @100%=145.9 W/Kg
Forward power=20 Watts
Reflected power=0 Watts
Heat-up time=50 Sec.s
Error range=2.4%

As shown in FIG. 5, the measurement boundaries were 10 cm. in the x direction and 0 to 2.0 cm in the y direction. The SAR gradient was 200% down to 20%. The rate of initial temperature rise is proportional with these SAR percentages. Thus, the helical coil type applicator provides the long, uniform shallow heat pattern desired for treating diseased tissue found to have spread around and along body passages.

Although a single embodiment of this invention has been described, it will be apparent to a person skilled in the art that various modifications to the details of construction shown and described may be made without departing from the scope of this invention.

What is claimed is:

1. An electromagnetic radiation applicator apparatus for treatment of benign prostatic hyperplasia comprising:

a catheter means for insertion into the urethra;
   an applicator means attached to the catheter means, said applicator means including an applicator and a connector means for connecting the applicator to a source of electromagnetic energy sufficient to elevate the temperature of tissue surrounding the applicator to a preselected temperature and for maintaining the preselected temperature during treatment;
   positioning means for positioning and maintaining the positioning of the catheter means in the urethra so that the applicator means attached to the catheter means is and remains positioned adjacent the prostate tissue to be treated for as long as desired by the user; and
   a temperature sensor supporting means attached to the catheter means for supporting a temperature sensing means in operative association with the applicator of the applicator means for measuring the temperature of the tissue surrounding the applicator.

2. An electromagnetic radiation applicator apparatus according to claim 1, wherein the catheter means has an end thereof adapted to extend from the urethra into the bladder when the catheter means is inserted into the urethra; wherein the positioning means includes an inflatable balloon mounted exteriorly of the catheter means on a portion thereof which extends into the bladder when the catheter means is positioned in the urethra; and a passage communicating with the balloon adapted to be connected to a source of pressurized fluid, whereby when the catheter means is positioned within the urethra, the balloon can be inflated within the bladder to engage the bladder opening to the urethra and position the catheter means.

3. An electromagnetic radiation applicator apparatus for treatment of benign prostatic hyperplasia comprising:

a catheter means for insertion into the urethra including a fluid free tube, a temperature sensor supporting tube, and an applicator support portion adjacent to a first end of the fluid free tube;

an applicator means including a coaxial cable mounted in the fluid free tube and an applicator mounted on the applicator support portion and connected to the coaxial cable for radiating electromagnetic energy into tissue adjacent to the applicator;

a temperature sensor means including a temperature sensor inserted in the temperature supporting tube for monitoring the temperature of the tissue adjacent to the applicator;

an electromagnetic energy generating means connected to the applicator means for supplying electromagnetic energy thereto;

a control means including a temperature reference means for setting a selected reference temperature to which the tissue is to be heated and a comparator connected to the temperature sensor means and temperature reference means for producing control signals; and said electromagnetic energy generating means being connected to the control means and responsive to the control signals for supplying electromagnetic energy to the applicator means sufficient to elevating the tissue temperature to the selected reference temperature and maintaining the tissue at the selected temperature during treatment.

4. An electromagnetic radiation applicator apparatus according to claim 2 wherein the applicator includes a helical coil type antenna.

5. An electromagnetic radiation applicator apparatus according to claim 2 wherein the applicator includes an elongated coil wrapped about the applicator support portion of the catheter means and the applicator means includes a sheath of dielectric material covering the elongated coil sufficiently for producing radiating energy levels along the elongated coil to maintain substantially uniform tissue temperature along the elongated coil.

6. An electromagnetic radiation applicator apparatus according to claim 2 wherein the catheter means includes means for maintaining the position of the applicator means during treatment of the prostate.

7. An electromagnetic radiation applicator apparatus according to claim 6 wherein the means for maintaining the position of the applicator means during treatment includes a fluid drainage tube, an inflatable balloon mounted exteriorly thereof and adjacent to a first end of the fluid drainage tube, and a pressurized fluid source connected to the balloon whereby, when the first end of the fluid drainage tube is positioned within a bladder opening and the balloon inflated, the balloon engages the bladder opening for fixing the location of the applicator means.

8. An electromagnetic radiation applicator apparatus according to claim 2 wherein the temperature sensor supporting tube includes an elongated tube having a closed end portion mounted exteriorly of the fluid free tube, and wherein the temperature sensor means includes a temperature sensor inserted in the elongated tube adjacent the applicator means for measuring the temperature of the tissue adjacent thereto.

9. An electromagnetic radiation applicator apparatus according to claim 2, wherein the catheter means includes a fluid drainage tube.

10. A urethral inserted applicator for benign prostatic hyperplasia treatment by heating the prostate tissue surrounding the urethra using electromagnetic energy comprising:

a multi-tube urinary catheter, said catheter having an insertion tip end for insertion into the urethra, a fluid dry tube closed at the insertion tip end, and an isolated open ended tube for urine drainage;

a coil type outwardly radiating antenna means including a coil mounted on the catheter and having an end toward the insertion tip end of the catheter, and a coaxial cable positioned in the fluid dry tube and having a center conductor and an outer conductor, the coil being connected to the center conductor of the coaxial cable at its end toward the insertion tip end of the catheter, and to the outer conductor of the coaxial cable at its end opposite the insertion tip end of the catheter; and dielectric insulation means covering the coil for preventing direct contact of the coil with the tissue.

11. A urethral inserted applicator according to claim 10, wherein the multi-tube urinary catheter further includes at least one additional fluid dry closed end tube, and at least one electromagnetic radiation compatible temperature sensor inserted in said at least one additional fluid dry closed tube for sensing the temperature of prostate tissue.

12. A urethral inserted applicator according to claim 8 wherein the coil has an open connection to the end of the coil toward the insertion tip end of the catheter and center coaxial conductor, an open connection to the end of the coil opposite the insertion tip end of the catheter and the outer coaxial conductor, and conductor gaps within the coil.

13. A urethral inserted applicator according to claim 10 wherein the coil has progressively increasing conductor width towards the insertion tip end of the catheter.

14. A urethral inserted applicator according to claim 10 wherein the coil has different turns ratio per unit length.

15. A urethral inserted applicator according to claim 10 wherein the center coaxial cable conductor extends through the center of the coil and wherein the diameter of the center coaxial cable conductor varies as it passes through the coil.

16. A urethral inserted applicator according to claim 10 wherein the thickness of the dielectric insulation means covering the coil varies along the length of the coil.

17. A system for controlling hyperthermia for benign prostatic hyperplasia comprising:
- a flexible catheter for insertion into the urethra, said catheter having an applicator means thereon for applying microwave energy to tissues of a prostate gland surrounding the urethra to thereby cause heating of said tissues and a microwave compatible temperature sensor for measuring the temperature of the heated tissues;
- a microwave generating means for producing microwaves having a preselected frequency, said microwave generating means being connected to the applicator means to supply microwave to the applicator means; and
- a comparator means interconnecting the microwave generating means and microwave compatible temperature sensor for comparing the measured temperature level to a preselected reference temperature level and outputting control signals to the microwave generating means for controlling the supply of microwave power to the applicator means to control the tissue temperature.

* * * * *

UNITED STATES PATENT AND TRADEMARK OFFICE
CERTIFICATE OF CORRECTION

PATENT NO.    : 4,967,765
DATED         : November 6, 1990
INVENTOR(S)   : Paul F. Turner, Theron N. Schaefermeyer, Amer M. Tumeh and Trung V. Nguyen It is certified that error appears in the above-identified patent and that said Letters Patent is hereby corrected as shown below:

Column 7,
Lines 51, 54 and 63, after "according to claim", please delete "2" insert -- 3 --.

Column 8,
Lines 10 and 18, after "according to claim", please delete "2" insert -- 3 --.
Lines 48-49, after "according to claim", please delete "8" insert -- 10 --.

Signed and Sealed this

Fifteenth Day of October, 2002

Attest:

JAMES E. ROGAN
Attesting Officer      Director of the United States Patent and Trademark Office